(12) United States Patent
Masaki et al.

(10) Patent No.: US 9,227,062 B2
(45) Date of Patent: Jan. 5, 2016

(54) SYSTEMS AND METHODS FOR SYNCHRONIZING AN OPERATION OF A MIDDLE EAR ANALYZER AND A COCHLEAR IMPLANT SYSTEM

(75) Inventors: Kinuko Masaki, San Francisco, CA (US); Abhijit Kulkarni, Newbury Park, CA (US); Aniket Saoji, Ann Arbor, MI (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/357,896

(22) PCT Filed: Nov. 15, 2011

(86) PCT No.: PCT/US2011/060728
§ 371 (c)(1),
(2), (4) Date: May 13, 2014

(87) PCT Pub. No.: WO2013/074085
PCT Pub. Date: May 23, 2013

(65) Prior Publication Data
US 2014/0309712 A1     Oct. 16, 2014

(51) Int. Cl.
*A61N 1/36* (2006.01)
*A61N 1/372* (2006.01)
*A61B 5/12* (2006.01)

(52) U.S. Cl.
CPC ........ *A61N 1/36032* (2013.01); *A61N 1/37235* (2013.01); *A61B 5/125* (2013.01)

(58) Field of Classification Search
CPC ............ A61N 1/0541; A61N 1/36032; A61N 1/37235; A61N 1/37241; A61B 5/12; A61B 5/121; A61B 5/125; A61B 5/126

USPC .......... 607/55–57, 136, 137; 600/559; 73/585
See application file for complete search history.

(56) References Cited

U.S. PATENT DOCUMENTS

| | | | |
|---|---|---|---|
| 5,626,629 A | 5/1997 | Faltys et al. | |
| 6,157,861 A * | 12/2000 | Faltys et al. | ..................... 607/57 |
| 6,208,882 B1 | 3/2001 | Lenarz et al. | |

(Continued)

FOREIGN PATENT DOCUMENTS

| | | |
|---|---|---|
| WO | WO-94/14376 | 7/1994 |
| WO | WO-97/09863 | 3/1997 |
| WO | WO-2011/038231 | 3/2011 |
| WO | WO-2011/069020 | 6/2011 |

OTHER PUBLICATIONS

International Search Report and Written Opinion received in International Application No. PCT/US11/060728, dated Jun. 27, 2012.

(Continued)

*Primary Examiner* — Eugene Wu
(74) *Attorney, Agent, or Firm* — ALG Intellectual Property, LLC

(57) ABSTRACT

An exemplary system for synchronizing an operation of a middle ear analyzer and a cochlear implant system includes 1) a mapping facility configured to maintain mapping data representative of an association between a plurality of sound levels and a plurality of current levels and between a plurality of frequencies and a plurality of electrodes, 2) a detection facility configured to receive an acoustic signal transmitted by the middle ear analyzer and detect a sound level and a frequency of the acoustic signal, and 3) a processing facility configured to identify, based on the mapping data, a current level associated with the detected sound level and one or more electrodes associated with the detected frequency and direct the cochlear implant system to apply electrical stimulation having the identified current level to one or more stimulation sites within a patient by way of the identified one or more electrodes.

18 Claims, 9 Drawing Sheets

(56) References Cited

U.S. PATENT DOCUMENTS

| | | | |
|---|---|---|---|
| 6,295,467 | B1 | 9/2001 | Kollmeier et al. |
| 7,117,038 | B1 | 10/2006 | Overstreet |
| 7,925,355 | B2 | 4/2011 | Quick |
| 2007/0179565 | A1 | 8/2007 | Overstreet et al. |
| 2008/0194984 | A1 | 8/2008 | Keefe |
| 2009/0018616 | A1 | 1/2009 | Quick et al. |
| 2010/0145177 | A1 | 6/2010 | Pau et al. |
| 2011/0137180 | A1 | 6/2011 | Johnson et al. |

OTHER PUBLICATIONS

Brickley, et al., "Investigations Into Electrically Evoked Stapedius Reflex Measures and Subjective Loudness Percepts in the MED-EL COMBI 40+ Cochlear Implant", *Cochlear Implants International*, 6(1), 31-42, 2005 Whurr Publishers Ltd.

MED-EL Corporation, "COMBI 40+ Cochlear Implant System", http://www.accessdata.fda.gov/cdrh_docs/pdf/P000025b.pdf, as accessed Feb. 18, 2014.

Gross, Aimee, "Fitting Techniques for the Pediatric Cochlear Implant Patient," http://www.audiologyonline.com/articles/fitting-techniques-for-pediatric-cochlear-1128, May 12, 2003.

Karatas, et al., "Intraoperative electrically evoked stapedius reflex thresholds in children undergone cochlear implantation: Round window and cochleostomy approaches", *International Journal of Pediatric Otorhinolaryngology*, vol. 75, Issue 9, Sep. 2011, pp. 1123-1126.

* cited by examiner

SYSTEMS AND METHODS FOR SYNCHRONIZING AN OPERATION OF A MIDDLE EAR ANALYZER AND A COCHLEAR IMPLANT SYSTEM

BACKGROUND INFORMATION

To overcome some types of hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant system is initially implanted in a patient, and during follow-up tests and checkups thereafter, it is usually necessary to fit the cochlear implant system to the patient. Such "fitting" includes adjustment of the base amplitude or intensity of the various stimuli generated by the cochlear implant system from the factory settings (or default values) to values that are most effective and comfortable for the patient. For example, the intensity or amplitude and/or duration of the individual stimulation pulses provided by the cochlear implant system may be mapped to an appropriate dynamic audio range so that the appropriate "loudness" of sensed audio signals is perceived. That is, loud sounds should be sensed by the patient at a level that is perceived as loud, but not painfully loud. Soft sounds should similarly be sensed by the patient at a level that is soft, but not so soft that the sounds are not perceived at all.

Hence, fitting and adjusting the intensity of the stimuli and other parameters of a cochlear implant system to meet a particular patient's needs requires the determination of one or more most comfortable current levels ("M levels"). An M level refers to a stimulation current level applied by a cochlear implant system at which the patient is most comfortable. M levels typically vary from patient to patient and from channel to channel in a multichannel cochlear implant.

M levels are typically determined based on subjective feedback provided by cochlear implant patients. For example, a clinician may present various stimuli to a patient and then analyze subjective feedback provided by the patient as to how the stimuli were perceived. Such subjective feedback typically takes the form of either verbal (adult) or non-verbal (child) feedback. Unfortunately, relying on subjective feedback in this manner is difficult, particularly for those patients who may have never heard sound before and/or who have never heard electrically-generated "sound." For young children, the problem is exacerbated by a short attention span, as well as difficulty in understanding instructions and concepts, such as high and low pitch, softer and louder, same and different. Moreover, many patients, such as infants and those with multiple disabilities, are completely unable to provide subjective feedback.

Hence, it is often desirable to employ an objective method of determining M levels for a cochlear implant patient. One such objective method involves applying electrical stimulation with a cochlear implant system to a patient until a stapedius reflex (i.e., an involuntary muscle contraction that occurs in the middle ear in response to acoustic and/or electrical stimulation) is elicited. This is because the current level required to elicit a stapedius reflex within a patient (referred to herein as a "stapedius reflex threshold") is highly correlated with (e.g., in many cases, substantially equal to) an M level corresponding to the patient. However, currently available techniques for measuring the current level at which a stapedius reflex actually occurs within a cochlear implant patient are unreliable, time consuming, and difficult to implement (especially with pediatric patients).

For example, a middle ear analyzer is often used to objectively measure a sound level at which an acoustic stimulus elicits a stapedius reflex in a non-cochlear implant patient by applying the acoustic stimulus to the ear of the non-cochlear implant patient and recording the resulting change in acoustic immittance. It would be desirable for a middle ear analyzer to be adapted for a cochlear implant patient by configuring the middle ear analyzer to record a change in acoustic immittance that occurs in response to electrical stimulation provided by the cochlear implant system. The change in the acoustic immittance could then be used to derive the stapedius reflex threshold.

However, it is currently difficult and time consuming for a clinician to use separate and unsynchronized devices to apply electrical stimulation and measure the resulting change in acoustic immittance. For example, the clinician may direct the cochlear implant system to step through a plurality of current levels as the middle ear analyzer records the resulting change in acoustic immittance. However, because the middle ear analyzer is not synchronized with the cochlear implant system (i.e., the middle ear analyzer does not "know" which current level is being applied by the cochlear implant system at any given time), it is impossible for the middle ear analyzer to correlate the recorded changes in acoustic immittance with the various current levels that are applied to the patient. Hence, the acoustic immittance recordings generated by the middle ear analyzer may be difficult or even impossible to interpret.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
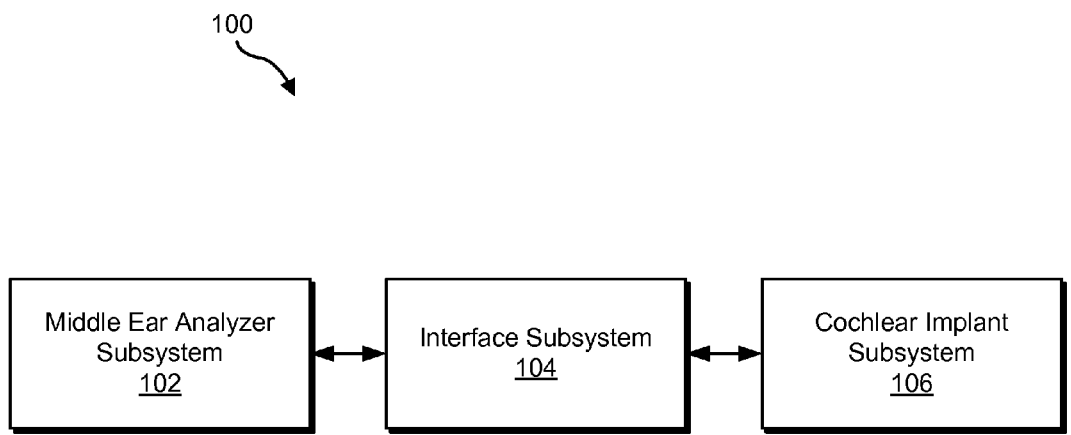
FIG. 1 illustrates an exemplary stapedius reflex elicitation and measurement system according to principles described herein.

Systems and methods of synchronizing an operation of a middle ear analyzer and a cochlear implant system are described herein. For example, an exemplary system may include a mapping facility, a detection facility, and a processing facility communicatively coupled one to another. The mapping facility may maintain mapping data representative of an association between a plurality of sound levels and a plurality of current levels and between a plurality of frequencies and a plurality of electrodes (e.g., a plurality of electrodes included on a lead configured to be implanted within a cochlea of a patient). The detection facility may receive an acoustic signal transmitted by a middle ear analyzer and detect a sound level and a frequency of the received acoustic signal. The processing facility may identify, based on the mapping data, a current level associated with the detected sound level and one or more electrodes associated with the detected frequency. The processing facility may then direct a cochlear implant system to apply electrical stimulation having the identified current level to one or more stimulation sites within a patient by way of the identified one or more electrodes.

The systems and methods described herein may be used to facilitate use of a middle ear analyzer in eliciting a stapedius reflex in a cochlear implant patient and determining a stapedius reflex threshold associated with the stapedius reflex (i.e., a current level at which the stapedius reflex occurs). For example, the systems and methods described herein may allow a middle ear analyzer to operate as it normally would (e.g., by generating an acoustic signal and increasing the sound level of the acoustic signal until a detected change in acoustic immittance indicates an occurrence of a stapedius reflex). However, instead of applying the acoustic signal directly to the patient, the acoustic signal is input into an interface unit implementing the systems and methods described herein. The interface unit converts the sound level and the frequency of the acoustic signal into a current level and one or more electrodes (i.e., one or more electrode numbers), respectively, and directs a cochlear implant system to apply electrical stimulation having the converted current level to one or more stimulation sites within a patient by way of the one or more electrodes. Hence, the change in acoustic immittance detected by the middle ear analyzer is actually in response to electrical stimulation representative of the acoustic signal, and not in direct response to the acoustic signal itself. However, because the operation of the middle ear analyzer and the cochlear implant system is synchronized (i.e., the cochlear implant system operates in response to and in accordance with acoustic signals provided by the middle ear analyzer), the detected change in acoustic immittance may be used to derive the stapedius reflex threshold (which, as described above, may be correlated with an M level of the patient).

The systems and methods described herein may be advantageous in settings in which a pediatric patient is being fitted with a cochlear implant system. As mentioned, pediatric patients have relatively short attention spans and are often incapable of providing subjective feedback. However, because the operation of the middle ear analyzer and the cochlear implant system is synchronized, the time required to acquire one or more stapedius reflex threshold values for a pediatric patient is greatly reduced compared to conventional stapedius reflex threshold acquisition techniques.

FIG. 1 illustrates an exemplary stapedius reflex elicitation and measurement system 100 (or simply "system 100"). System 100 may be configured to elicit one or more stapedius reflexes within a cochlear implant patient and identify one or more current levels at which the one or more stapedius reflexes occur. To this end, system 100 may include a middle ear analyzer subsystem 102, an interface subsystem 104, and a cochlear implant system 106 communicatively coupled to one another. Each of these subsystems may alternatively be referred to herein as "systems" and will now be described in connection with FIGS. 2-4.

Figure 2:
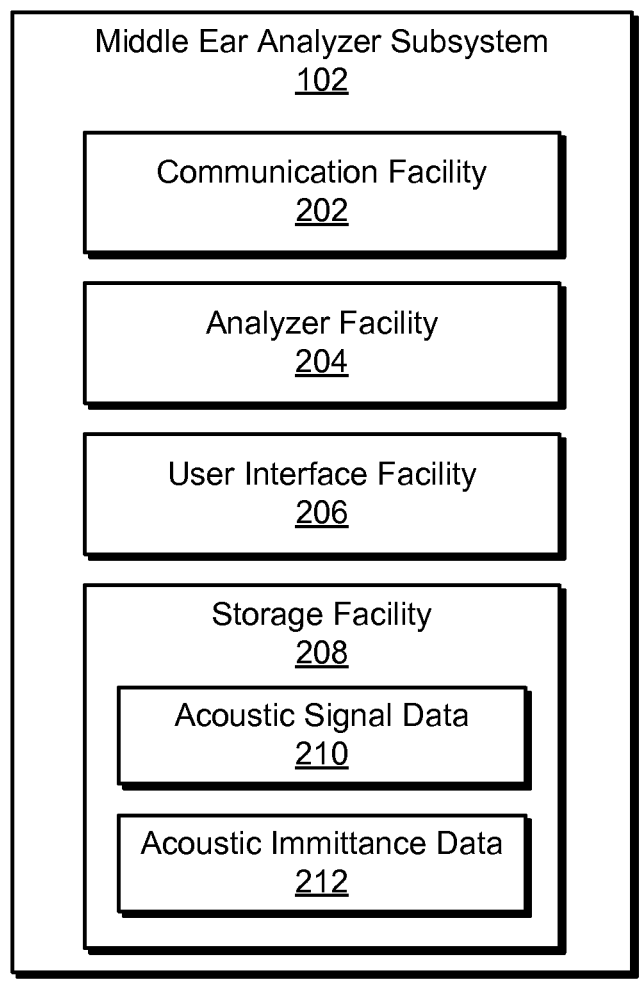
FIG. 2 shows various components of a middle ear analyzer subsystem according to principles described herein.

FIG. 2 shows various components of middle ear analyzer subsystem 102. As shown, middle ear analyzer subsystem 102 may include, without limitation, a communication facility 202, an analyzer facility 204, a user interface facility 206, and a storage facility 208 communicatively coupled to one another. It will be recognized that although facilities 202-208 are shown to be separate facilities in FIG. 2, any of facilities 202-208 may be combined into fewer facilities, such as into a single facility, or divided into more facilities as may serve a particular implementation.

Communication facility 202 may be configured to facilitate communication between middle ear analyzer subsystem 102 and interface subsystem 104. For example, communication facility 202 may be implemented by a probe configured to be communicatively coupled to interface subsystem 104. Communication facility 202 may additionally or alternatively be configured to facilitate data transmission between middle ear analyzer subsystem 102 and interface subsystem 104.

Analyzer facility 204 may be configured to perform one or more middle ear analysis functions. For example, analyzer facility 204 may be configured to generate and transit an acoustic signal to interface subsystem 104. As will be described in more detail below, interface subsystem 104 may direct cochlear implant subsystem 106 to apply electrical stimulation representative of the acoustic signal to one or more stimulation sites within a patient (e.g., one or more stimulation sites along an auditory pathway of the patient).

Analyzer facility 204 may be further configured to measure and record a change in acoustic immittance that occurs in response to application of the electrical stimulation representative of the acoustic signal. As used herein, "acoustic immittance" may refer to an acoustic impedance, admittance, and/or combination thereof. For example, acoustic immittance may refer to a ratio of sound pressure to volume velocity within the ear canal that occurs in response to application of electrical and/or acoustic stimulation of the auditory pathway of the patient.

In some examples, analyzer facility 204 may be configured to increase the sound level of the acoustic signal provided to interface facility 104 until analyzer facility 204 detects a change in the acoustic immittance that indicates an occurrence of a stapedius reflex. This may be performed in any suitable manner. For example, analyzer facility 204 may increase the sound level of the acoustic signal until the change in acoustic immittance reaches a predetermined threshold.

Additionally or alternatively, analyzer facility 204 may be configured to increase the sound level of the acoustic signal until the sound level is equal to a predetermined maximum threshold level (e.g., an "uncomfortable level" or "U level" of a cochlear implant patient). The U level of a cochlear implant patient may be determined in any suitable manner. As will be described below, a clinician may analyze the resultant acoustic immittance data and thereby determine whether a stapedius reflex occurred at some point during the increase in the sound level of the acoustic signal.

In some examples, analyzer facility 204 may be configured to detect multiple stapedius reflexes associated with the patient during a single analysis session. For example, analyzer facility 204 may be configured to sequentially generate and transmit multiple acoustic signals each having a distinct frequency. Analyzer facility 204 may sweep through a plurality of sound levels for each acoustic signal until a stapedius reflex is detected for each of the acoustic signals.

User interface facility 206 may be configured to provide one or more graphical user interfaces ("GUIs") associated with an operation of middle ear analyzer subsystem 102. For example, a GUI may be provided and configured to facilitate user input identifying various frequencies and sound levels that the clinician desires to test with a particular patient. Additionally or alternatively, as will be illustrated below, user interface facility 206 may be configured to present a graph representative of the change in acoustic immittance that occurs as a sound level of an acoustic signal is increased.

Storage facility 208 may be configured to maintain acoustic signal data 210 representative of one or more acoustic signals generated by analyzer facility 204 and acoustic immittance data 212 representative of one or more acoustic immittance measurements made by analyzer facility 204. It will be recognized that storage facility 208 may maintain additional or alternative data as may serve a particular implementation.

Figure 3:
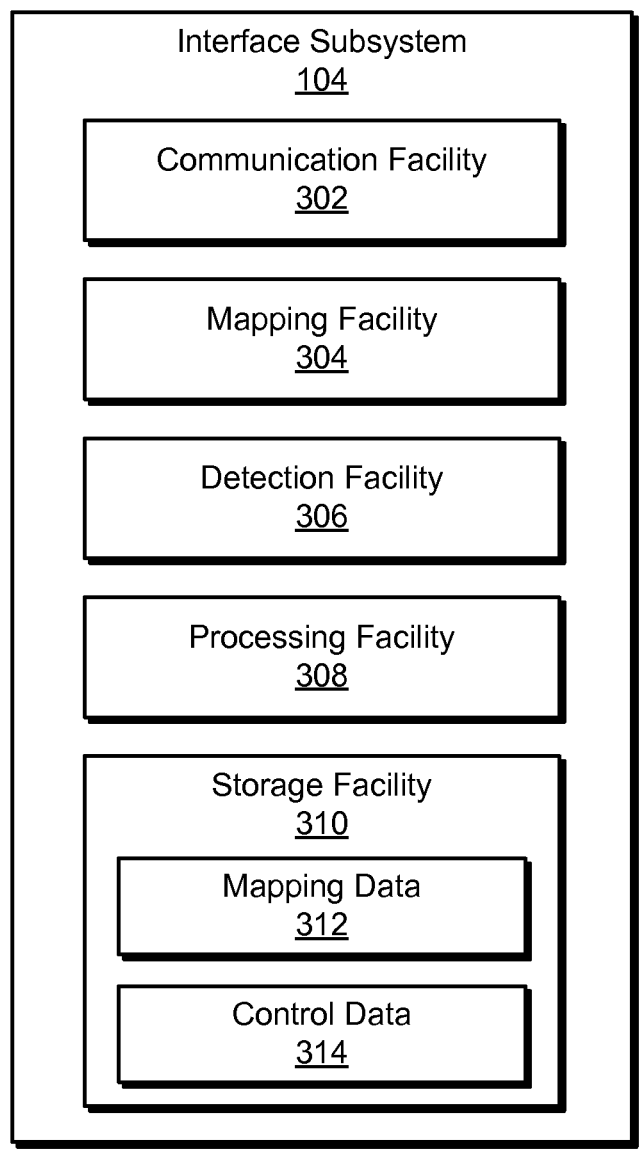
FIG. 3 shows various components of an interface subsystem according to principles described herein.

FIG. 3 shows various components of interface subsystem 104. As shown, interface subsystem 104 may include, without limitation, a communication facility 302, a mapping facility 304, a detection facility 306, a processing facility 308, and a storage facility 310 communicatively coupled to one another. It will be recognized that although facilities 302-310 are shown to be separate facilities in FIG. 3, any of facilities 302-310 may be combined into fewer facilities, such as into a single facility, or divided into more facilities as may serve a particular implementation.

Communication facility 302 may be configured to facilitate communication between interface subsystem 104 and middle ear analyzer subsystem 102. Communication facility 302 may be further configured to facilitate communication between interface subsystem 104 and cochlear implant subsystem 106. To this end, communication facility 302 may be configured to employ any suitable combination of ports, communication protocols, and data transmission means.

Mapping facility 304 may be configured to manage (e.g., maintain, generate, update, etc.) mapping data representative of an association between a plurality of sound levels and a plurality of current levels and between a plurality of frequencies and a plurality of electrodes. Mapping data may be maintained in the form of a look-up table, in a database, and/or in any other manner as may serve a particular implementation.

To illustrate, Table 1 illustrates mapping data representative of an exemplary association between a plurality of sound levels and a plurality of current levels that may be maintained by mapping facility 304.

TABLE 1

| Sound Level (dB SPL) | Current Level (CU) |
| --- | --- |
| 80 | 110 |
| 85 | 120 |
| 90 | 130 |
| 95 | 140 |
| 100 | 150 |

As shown in Table 1, the mapping data indicates that a sound level of 80 dB SPL is mapped to a current level of 110 clinical units ("CU"), a sound level of 85 dB SPL is mapped to a current level of 120 CU, a sound level of 90 DB SPL is mapped to a current level of 130 CU, a sound level of 95 dB SPL is mapped to a current level of 140 CU, and a sound level of 100 dB SPL is mapped to a current level of 150 CU. As will be described below, processing facility 308 may use the mapping data illustrated in Table 1 to identify a current level that is associated with a sound level of a particular acoustic signal detected by detection facility 306. It will be recognized that the mapping associations between current level and sound level illustrated in Table 1 are merely illustrative of the many different mapping associations that may be utilized in accordance with the systems and methods described herein.

Table 2 illustrates additional mapping data representative of an exemplary association between a plurality of frequencies and a plurality of electrodes (e.g., a plurality of electrodes included on a lead configured to be implanted within a cochlea of a patient) that may be maintained by mapping facility 304.

TABLE 2

| Frequency (kHz) | Electrode Numbers |
| --- | --- |
| 1 | 1-4 |
| 2 | 5-8 |
| 3 | 9-12 |
| 4 | 13-16 |

As shown in Table 2, the additional mapping data indicates that a frequency of 1 kHz is mapped to electrodes 1 through 4, a frequency of 2 kHz is mapped to electrodes 5 through 8, a frequency of 3 kHz is mapped to electrodes 9 through 12, and a frequency of 4 kHz is mapped to electrodes 13 through 16. As will be described below, processing facility 308 may use the mapping data illustrated in Table 2 to identify one or more electrodes that are associated with a frequency of a particular acoustic signal detected by detection facility 306. It will be recognized that the mapping associations between frequency and electrode numbers illustrated in Table 2 are merely illustrative of the many different mapping associations that may be utilized in accordance with the systems and methods described herein.

Detection facility 306 may be configured to receive one or more acoustic signals transmitted by a middle ear analyzer subsystem 102 and detect a sound level and frequency of the one or more acoustic signals. Detection facility 306 may employ any suitable signal processing heuristic to detect the sound level and frequency of an acoustic signal as may serve a particular implementation.

Processing facility 308 may be configured to perform any suitable processing operation related to one or more acoustic signals detected by detection 306. For example, processing facility 308 may use the mapping data maintained by mapping facility 304 to identify a current level associated with a sound level of an acoustic signal as detected by detection facility 306. To illustrate, detection facility 306 may determine that a particular acoustic signal has a sound level of 90 dB SPL. Using the mapping data illustrated in Table 1, processing facility 308 may determine that a current level of 130 CU is associated with the 90 dB SPL sound level.

Additionally or alternatively, processing facility 308 may use the mapping data maintained by mapping facility 304 to identify one or more electrodes associated with a frequency of an acoustic signal as detected by detection facility 306. To illustrate, detection facility 306 may determine that a particular acoustic signal has a frequency of 2 kHz. Using the mapping data illustrated in Table 2, processing facility 308 may determine that electrodes 5 through 8 are associated with the 2 kHz frequency.

Once processing facility 308 has identified a current level associated with a sound level of a detected acoustic signal and one or more electrodes associated with a frequency of the detected acoustic signal, processing facility 308 may direct a cochlear implant system (e.g. cochlear implant subsystem 106) to apply electrical stimulation having the identified current level to one or more stimulation sites within the patient by way of the identified one or more electrodes.

To illustrate, processing facility 308 may transmit control data representative of the identified current level and the identified one or more electrodes to a sound processor included within the cochlear implant system. The sound processor may then utilize the received control data to direct a cochlear implant to generate and apply the electrical stimulation having the identified current level by way of the identified one or more electrodes. For example, if the acoustic signal has a sound level of 90 dB SPL and a frequency of 2 kHz, the sound processor may direct the cochlear implant to generate and apply electrical stimulation having a current level of 130 CU by way of electrodes 5 through 8.

As mentioned, middle ear analyzer subsystem 102 may be configured to increase the sound level of an acoustic signal either until a stapedius reflex is detected or until the sound level is equal to a predetermined maximum threshold level (e.g., a U level). In some examples, detection facility 306 may detect the increase in the sound level of the acoustic signal and processing facility 308 may direct the cochlear implant system to dynamically increase the current level of the electrical stimulation in response to the increase in the sound level and in accordance with the mapping data maintained by mapping facility 304.

To illustrate, middle ear analyzer subsystem 102 may be configured to increase a sound level of an acoustic signal by stepping or sweeping through at least some of the sound levels listed in Table 1. For example, the sound level of an acoustic signal transmitted by middle ear analyzer subsystem 102 may initially be equal to 80 dB SPL. After a predetermined period of time (e.g., a few seconds), middle ear analyzer subsystem 102 may increase the sound level of the acoustic signal being transmitted to 85 dB SPL. After another predetermined period of time, middle ear analyzer subsystem 102 may increase the sound level of the acoustic signal being transmitted to 90 dB SPL. This incremental increase in sound level may continue until a stapedius reflex is detected or until the sound level is equal to a predetermined maximum threshold level. Detection facility 306 may detect each incremental increase in sound level and processing facility 308 may use the mapping data (e.g., the mapping data shown in Table 1) to identify a current level associated with each new sound level. Each time processing facility 308 identifies a new current level, processing facility 308 may direct the cochlear implant system to dynamically increase the current level of the electrical stimulation to be equal to the identified current level.

In some examples, processing facility 308 may be configured to prevent the cochlear implant system from increasing the current level of the electrical stimulation applied to the patient beyond a U level associated with the patient. As mentioned, the U level represents an "uncomfortable level" associated with the patient. Stimulation above the U level may result in discomfort, pain, and/or damage to the patient. Hence, limiting the cochlear implant system from increasing the current level beyond the U level of a patient may ensure patient comfort and safety.

Processing facility 308 may be further configured to present one or more GUIs and receive user input by way of the one or more GUIs. For example, processing facility 308 may be configured to detect an occurrence of a stapedius reflex and designate the current level associated with the stapedius reflex as being an M level associated with the patient. The detection of the occurrence of the stapedius reflex may be performed automatically by processing facility 308 or in response to user input provided by way of one or more GUIs presented by processing facility 308. For example, processing facility 308 may receive user input representative of a sound level at which a stapedius reflex occurred during the application of electrical stimulation by the cochlear implant system. Based on the user input and on the mapping data, processing facility 308 may determine a current level at which the stapedius reflex occurred, designate the current level as an M level associated with the patient, and present data representative of the M level within a GUI. An example of this will be provided in more detail below.

As another example, processing facility 308 may present a GUI configured to facilitate user customization of the mapping data maintained by mapping facility 304. For example, processing facility 308 may present a GUI configured to allow a user to edit the mapping data illustrated in Table 1 and/or Table 2 as shown above. In this manner, a clinician may modify one or more mapping associations as may serve a particular implementation.

Processing facility 308 may be further configured to perform one or more calibration operations associated with a particular middle ear analyzer. For example, interface subsystem 104 may be used in connection with a variety of different middle ear analyzers. Each middle ear analyzer may be calibrated upon being connected to interface subsystem 104 so that appropriate current levels are applied to the patient.

In some alternative examples, it may be desirable for a user of interface subsystem 104 to specify a particular group of electrodes to be tested (i.e., a group of electrodes for which a stapedius reflex threshold is to be determined). For example, a clinician may desire to determine the M level for a single electrode. To this end, processing facility 308 may provide a GUI configured to facilitate identification by a user of one or more specific electrodes. In response to receiving this user input, processing facility 308 may direct middle ear analyzer subsystem 102 to provide an acoustic signal having a frequency associated with the identified one or more electrodes. Detection facility 306 may detect the sound level of an acoustic signal, and processing facility 308 may identify a current level associated with the sound level based on the mapping data. Processing facility 308 may then direct a cochlear implant system to apply electrical stimulation having the identified current level by way of the identified one or more electrodes.

Storage facility 310 may be configured to maintain mapping data 312 managed by mapping facility 304 and control data 314 generated by processing facility 308. It will be recognized that storage facility 310 may maintain additional or alternative data as may serve a particular implementation.

Figure 4:
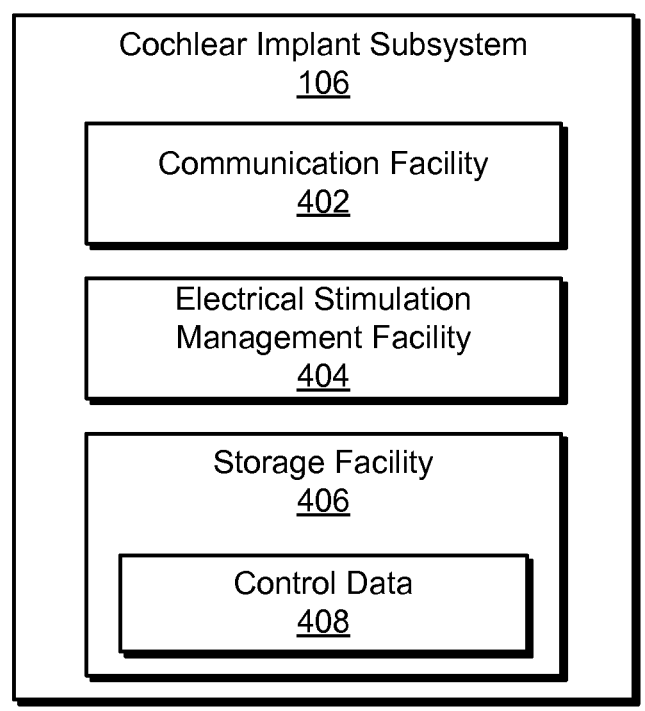
FIG. 4 shows various components of a cochlear implant subsystem according to principles described herein.

FIG. 4 shows various components of cochlear implant subsystem 106. As shown, cochlear implant subsystem 106 and may include, without limitation, a communication facility 402, an electrical stimulation management facility 404, and a storage facility 406 communicatively coupled to one another. It will be recognized that although facilities 402-406 are shown to be separate facilities in FIG. 4, any of facilities 402-406 may be combined into fewer facilities, such as into a single facility, or divided into more facilities as may serve a particular implementation.

Communication facility 402 may be configured to facilitate communication between cochlear implant subsystem 106 and interface subsystem 104. To this end, communication facility 402 may be configured to employ any suitable combination of ports, communication protocols (e.g., wired and/or wireless communication protocols), and data transmission means.

Electrical stimulation management facility 404 may be configured to perform any suitable electrical stimulation operation as may serve a particular implementation. For example, electrical stimulation management facility 404 may receive control data representative of a particular current level and one or more electrodes from interface subsystem 104. Based on this control data, electrical stimulation management facility 404 may generate and apply electrical stimulation having the particular current level to one or more stimulation sites within a cochlear implant patient by way of the one or more electrodes. The electrical stimulation may be generated and applied in any suitable manner as may serve a particular implementation. For example, a sound processor located external to the patient may use the control data to generate one or more stimulation parameters configured to direct a cochlear implant implanted within the patient to generate and apply the electrical stimulation.

Storage facility 406 may be configured to maintain control data 408 received from interface subsystem 104. It will be recognized that storage facility 406 may maintain additional or alternative data as may serve a particular implementation.

Figure 5:
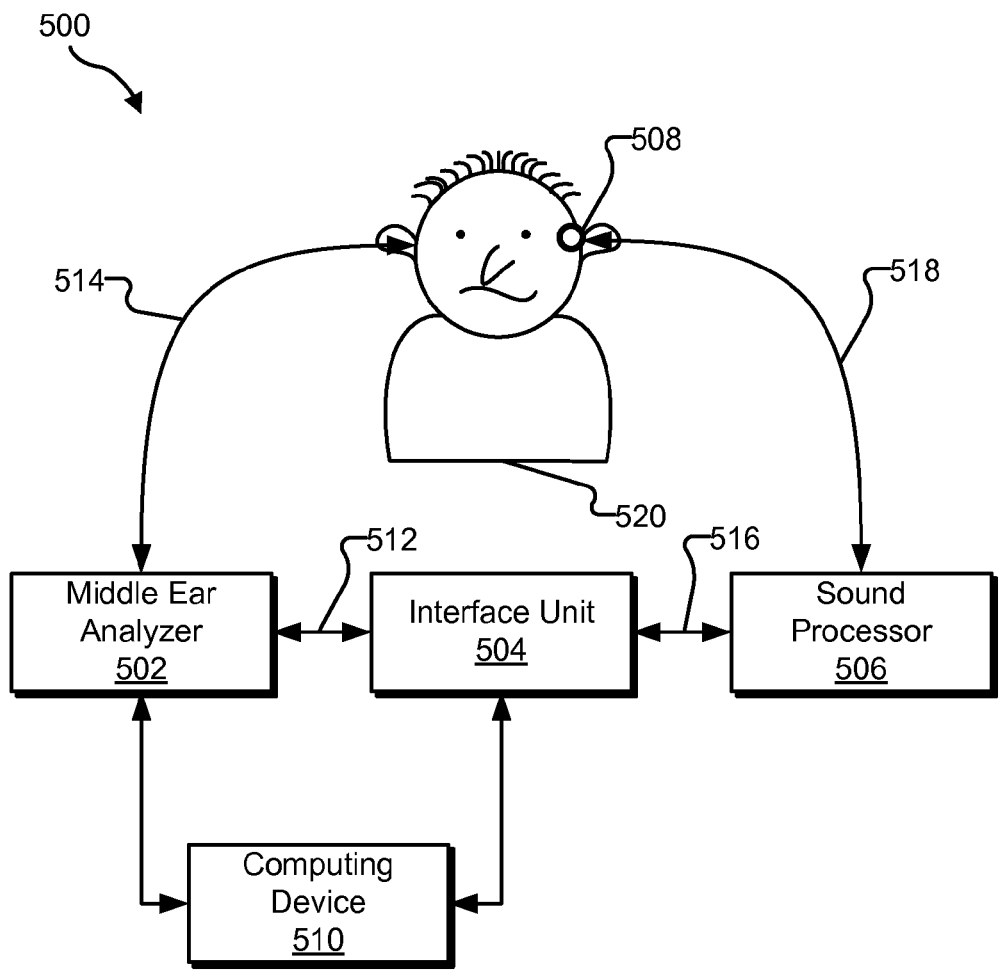
FIG. 5 illustrates an exemplary implementation of the system of FIG. 1 according to principles described herein.

FIG. 5 illustrates an exemplary implementation 500 of system 100. As shown, implementation 500 may include a middle ear analyzer 502, an interface unit 504, a sound processor 506, a cochlear implant 508, and a computing device 510. Implementation 500 may further include a stimulation probe 512 configured to communicatively couple middle ear analyzer 502 and interface unit 504 and a detection probe 514 configured to be coupled to middle ear analyzer 502 and detect a change in immittance that occurs as a result of electrical stimulation applied by way of one or more electrodes (not shown) communicatively coupled to cochlear implant 508.

Middle ear analyzer subsystem 102, interface subsystem 104, and cochlear implant subsystem 106 may each be implemented by one or more components illustrated in FIG. 5. For example, middle ear analyzer subsystem 102 may be implemented by a middle ear analyzer 502, stimulation probe 512, detection probe 514, and computing device 510. Interface subsystem 104 may be implemented by interface unit 504 and computing device 510. Cochlear implant subsystem 106 may be implemented by sound processor 506 and cochlear implant 508.

Each of the components shown in FIG. 5 will now be described in more detail. Middle ear analyzer 502 may include any suitable middle ear analyzer (e.g. an off-the-shelf middle ear analyzer) configured to perform one or more of the middle ear analyzer operations described herein. For example, middle ear analyzer 502 may be configured to operate in a contralateral stimulation mode in which middle ear analyzer 502 is configured to generate and apply acoustic stimulation (i.e., one or more acoustic signals) by way of stimulation probe 512 and record a resulting change in immittance using detection probe 514.

Interface unit 504 may be configured to perform one or more interface operations as described herein. For example, interface unit 504 may include any combination of signal receivers, signal transmitters, processors, and/or computing devices configured to receive an acoustic signal transmitted by a middle ear analyzer 502 by way of stimulation probe 512, detect a sound level and frequency of the acoustic signal, and transmit control data representative of a current level associated with the sound level and one or more electrodes associated with the frequency to sound processor 506.

Interface unit 504 may be coupled directly to middle ear analyzer 502 by way of stimulation probe 512. Interface unit 504 may also be coupled to sound processor 506 by way of communication channel 516, which may include any suitable wired and/or wireless communication channel as may serve a particular implementation.

Sound processor 506 may include any type of sound processor used in a cochlear implant system as may serve a particular implementation. For example, sound processor 506 may include a behind-the-ear ("BTE") sound processing unit, a portable speech processor ("PSP"), and/or a body-worn processor.

Cochlear implant 508 may include any suitable auditory prosthesis configured to be at least partially implanted within a patient as may serve a particular implementation. For example, cochlear implant 508 may include an implantable cochlear stimulator, a brainstem implant and/or any other type of auditory prosthesis. In some examples, cochlear implant 508 may be communicatively coupled to a lead having a plurality of electrodes (e.g., sixteen electrodes) disposed thereon. The lead may be configured to be implanted within the patient such that the electrodes are in communication with stimulation sites (e.g., locations within the cochlea) within the patient. As used herein, the term "in communication with" refers to an electrode being adjacent to, in the general vicinity of, in close proximity to, directly next to, or directly on a stimulation site.

Sound processor 506 and cochlear implant 508 may communicate by way of communication channel 518. Communication channel 518 may be wired or wireless as may serve a particular implementation.

Computing device 510 may include any combination of computing devices (e.g., personal computers, mobile computing devices (e.g., mobile phones, tablet computers, laptop computers, etc.), fitting stations, etc.). As shown, computing device 510 may be communicatively coupled (e.g., with one or more cables) to both the middle ear analyzer 502 and the interface unit 504. As such, computing device 510 may be configured to perform one or more of the operations associated with the middle ear analyzer 502 and the interface unit 504. For example, computing device 510 may generate and present one or more GUIs by way of a display device (e.g., a display screen included within computing device 510 and/or communicatively coupled to computing device 510) associated with an operation of middle ear analyzer 502 and/or interface unit 504.

Additionally or alternatively, computing device 510 may be configured to store, maintain, process, and/or otherwise maintain the mapping data utilized by interface subsystem 104. For example, computing device 510 may be configured to maintain a database comprising the mapping data and identify current levels and/or electrodes associated with an acoustic signal received by interface unit 504.

In some alternative examples, separate computing devices may be associated with middle ear analyzer 502 and interface unit 504. For example, a first computing device may be communicatively coupled to middle ear analyzer 502 and configured to perform one or more operations associated with middle ear analyzer 502 and a second computing device may be communicatively coupled to interface unit 504 and configured to perform one or more operations associated with interface unit 504.

In yet another alternative example, interface unit 504 may not be coupled to computing device 510 or to any other computing device. In this example, interface unit 504 may be configured to perform all of the operations associated with interface subsystem 104 as described herein.

In an exemplary configuration, detection probe 514 is placed within one of the ears of a patient 520. In some examples, as shown in FIG. 5, the ear in which detection probe 514 is placed is contralateral to the ear associated with cochlear implant 508. Alternatively, detection probe 514 may be placed within the same ear associated with cochlear implant 508.

Figure 6:
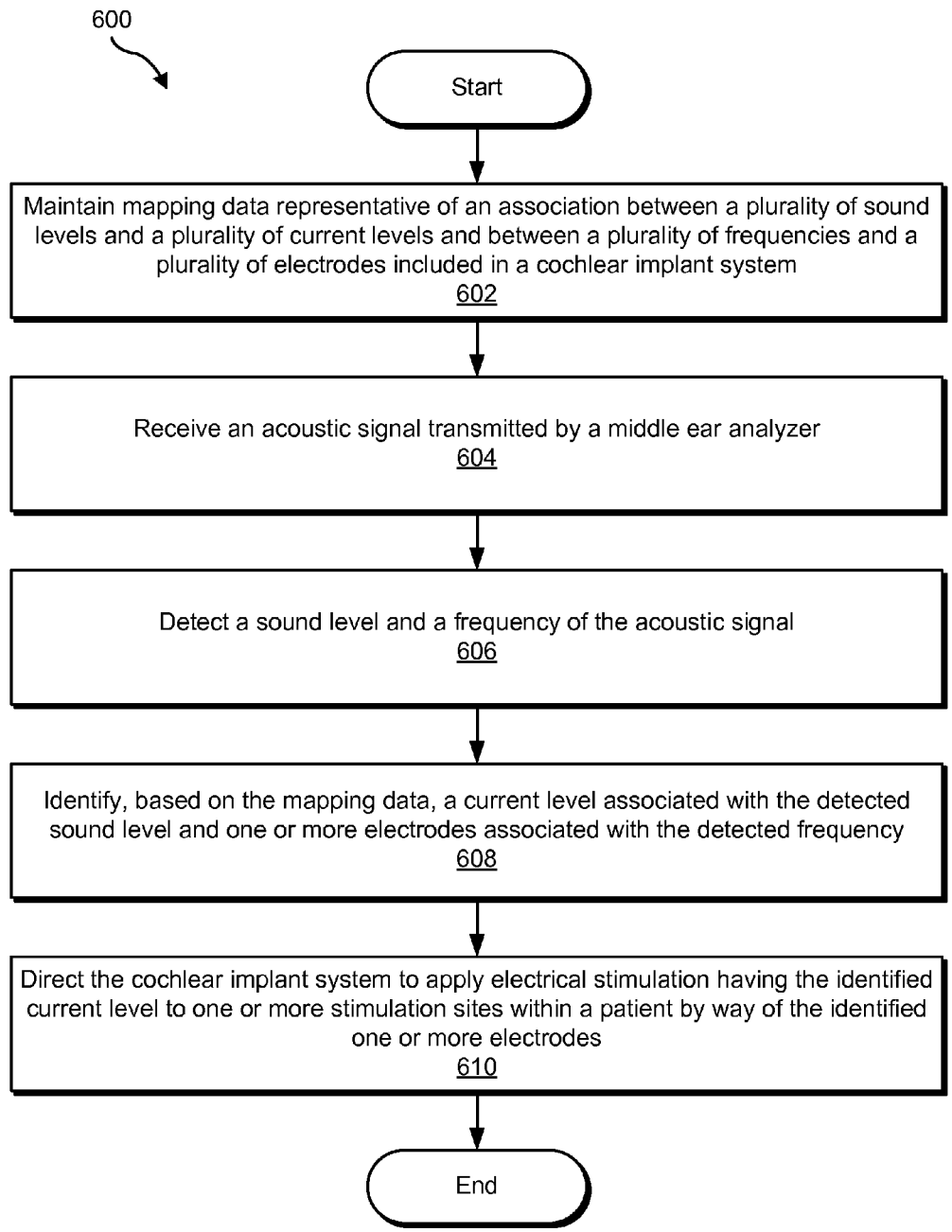
FIG. 6 illustrates an exemplary method of synchronizing an operation of a middle ear analyzer and a cochlear implant system according to principles described herein.

FIG. 6 illustrates an exemplary method 600 of synchronizing an operation of a middle ear analyzer and a cochlear implant system. While FIG. 6 illustrates exemplary steps according to one embodiment, other embodiments may omit, add to, reorder, and/or modify any of the steps shown in FIG. 6. One or more of the steps shown in FIG. 6 may be performed by interface subsystem 104 and/or any implementation thereof.

In step 602, an interface subsystem maintains mapping data representative of an association between a plurality of sound levels and a plurality of current levels and between a plurality of frequencies and a plurality of electrodes included in the cochlear implant system. Step 602 may be performed in any of the ways described herein.

In step 604, the interface subsystem receives an acoustic signal transmitted by the middle ear analyzer. Step 604 may be performed in any of the ways described herein.

In step 606, the interface subsystem detects a sound level and a frequency of the acoustic signal. Step 606 may be performed in any of the ways described herein.

In step 608, the interface subsystem identifies, based on the mapping data, a current level associated with the detected sound level and one or more electrodes associated with the detected frequency. Step 608 may be performed in any of the ways described herein.

In step 610, the interface subsystem directs the cochlear implant system to apply electrical stimulation having the identified current level to one or more stimulation sites within a patient by way of the identified one or more electrodes. Step 610 may be performed in any of the ways described herein.

An example of the systems and methods described herein will now be provided. It will be recognized that this example is merely illustrative of the many different implementations that may be realized in accordance with the systems and methods described herein.

In this example, a clinician may desire to determine a plurality of M levels associated with a cochlear implant patient (e.g., a pediatric cochlear implant patient). To this end, the clinician may utilize the configuration shown in FIG. 5. For example, the clinician may program middle ear analyzer 502 to operate in a contralateral stimulation mode, program the middle ear analyzer 502 (e.g., by way of one or more GUIs presented by computing device 510) with a desired frequency range, sound level range, and sound level step size. To illustrate, the clinician may program middle ear analyzer 502 to step through each of the sound levels shown in Table 1 for each of the frequencies shown in Table 2 until a stapedius reflex is detected or until the sound level is equal to a predetermined maximum threshold level (e.g., a U level).

The clinician may place probe 514 within one of the ears of the patient and ensure that probe 512 is connected to interface unit 504 and that interface unit 504 is in turn connected to sound processor 506. The clinician may then initiate an analysis session (e.g., by pressing "start" on middle ear analyzer 502). In response, middle ear analyzer 502 may automatically generate and transmit acoustic signals to interface unit 504 in accordance with the programmed frequency range, sound level range, and sound level step size. As described above, interface unit 504 (and, in some implementations, computing device 510) may direct sound processor 506 and cochlear implant 508 to generate and apply electrical stimulation representative of the acoustic signals to the patient. Middle ear analyzer 502 may record the various changes in acoustic immittance that occur as a result of the electrical stimulation.

In some examples, middle ear analyzer subsystem 102 (i.e., middle ear analyzer 502 and/or computing device 510) may present a graph representative of the changes in acoustic immittance that occur as a result of the electrical stimulation provided by cochlear implant 508. In this manner, the clinician may visually identify one or more sound levels at which one or more stapedius reflexes occur.

Figure 7:
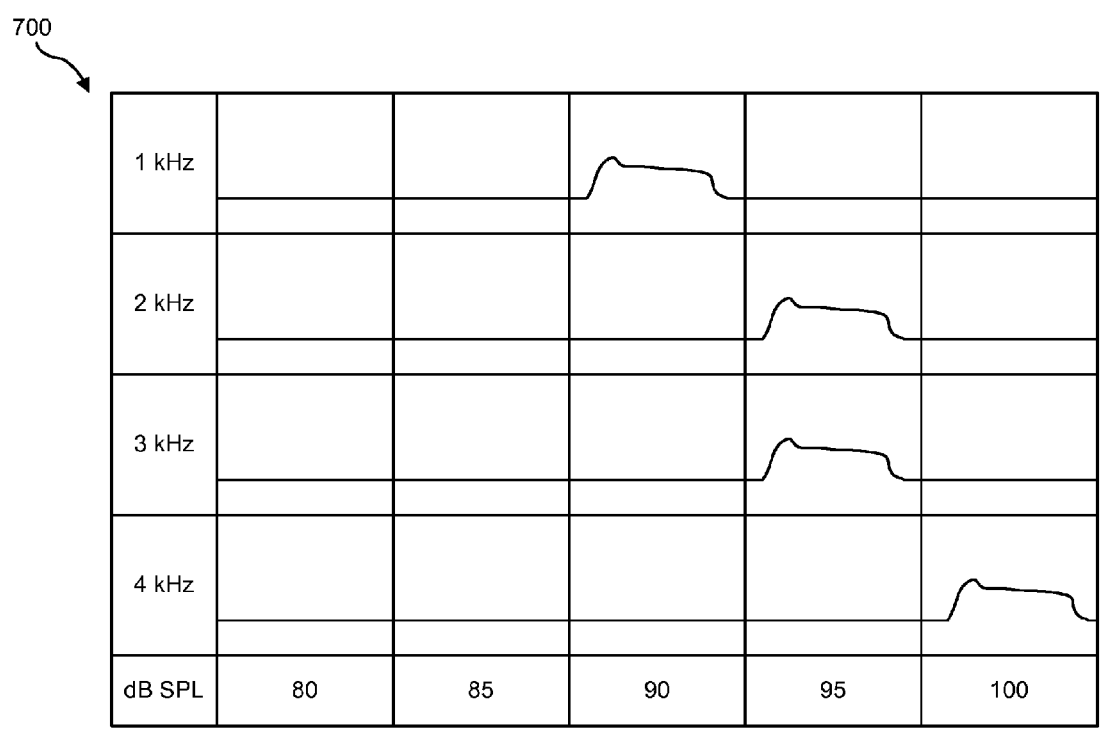
FIGS. 7-8 show exemplary graphical user interfaces ("GUIs") that may be presented according to principles described herein.

To illustrate, FIG. 7 shows an exemplary GUI 700 that may be presented by middle ear analyzer subsystem 102. As shown, GUI 700 includes a graph representative of a change in acoustic immittance that occurs as the sound level is increased for each acoustic signal generated by middle ear analyzer 502 (i.e., for each frequency listed in Table 2). By viewing GUI 700, a clinician may visually determine a sound level at which a stapedius reflex occurs for each frequency. For example, the clinician may visually identify a sound level at which the change in acoustic immittance is above a certain threshold (e.g., a sound level at which a peak in the change in acoustic immittance occurs). To illustrate, a clinician may determine that a stapedius reflex occurred at a sound level of 90 dB SPL for the 1 kHz acoustic signal, at 95 dB SPL for the 2 kHz and 3 kHz acoustic signals, and at 100 dB SPL for the 4 kHz acoustic signal.

Figure 8:
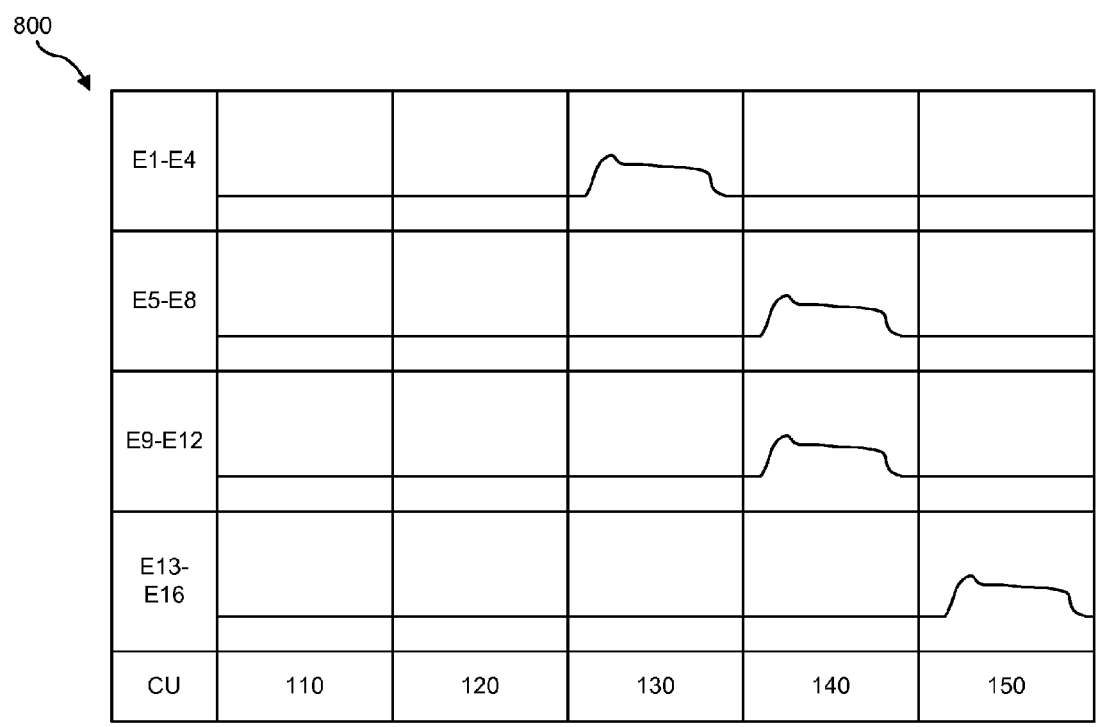

In some examples, middle ear analyzer subsystem 102 and/or interface subsystem 104 may automatically convert the acoustic values shown in FIG. 7 to corresponding electrical values. This may be performed in response to a user input command, for example, and may facilitate visual identification of the current levels that elicit the various stapedius reflexes. For example, FIG. 8 shows an exemplary GUI 800 that may be presented to a user and that may allow the user to determine stapedius reflex thresholds (and, therefore, M levels) for each of the electrodes to which electrical stimulation was applied. To illustrate, a clinician may determine that a stapedius reflex occurred at 130 CU for electrodes 1-4 and designate 130 CU as the M level for those electrodes. GUI 800 may be generated based on the mapping data maintained by interface subsystem 104.

Interface subsystem 104 may present data representative of one or more stapedius reflex thresholds in any other manner as may serve a particular implementation. For example, interface subsystem 104 may provide a GUI configured to receive user input representative of the sound levels at which the various stapedius reflexes illustrated in FIG. 7 occurred. For example, a clinician may enter a value 90 dB SPL for the 1 kHz acoustic signal into the GUI. Interface subsystem 104 may convert the entered value into a current level in accordance with the mapping data and then present the converted current level within the GUI. For example, interface subsystem 104 may convert the 90 dB SPL value into 130 CU and then display a value of 130 CU within the GUI.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 9:
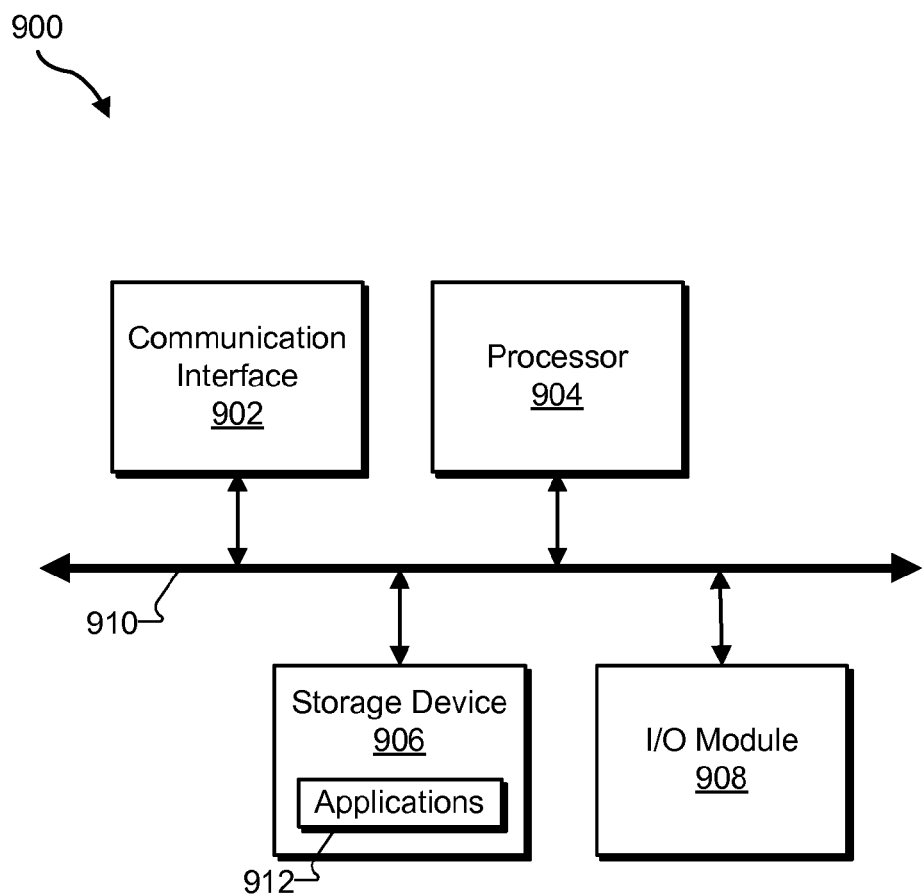
FIG. 9 illustrates an exemplary computing device according to principles described herein.

FIG. 9 illustrates an exemplary computing device 900 that may be configured to perform one or more of the processes described herein. As shown in FIG. 9, computing device 900 may include a communication interface 902, a processor 904, a storage device 906, and an input/output ("I/O") module 908 communicatively connected via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, an audio/video connection, and any other suitable interface.

Processor 904 generally represents any type or form of processing unit capable of processing data or interpreting, executing, and/or directing execution of one or more of the instructions, processes, and/or operations described herein. Processor 904 may direct execution of operations in accordance with one or more applications 912 or other computer-executable instructions such as may be stored in storage device 906 or another computer-readable medium.

Storage device 906 may include one or more data storage media, devices, or configurations and may employ any type, form, and combination of data storage media and/or device. For example, storage device 906 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 906. For example, data representative of one or more executable applications 912 configured to direct processor 904 to perform any of the operations described herein may be stored within storage device 906. In some examples, data may be arranged in one or more databases residing within storage device 906.

I/O module 908 may be configured to receive user input and provide user output and may include any hardware, firmware, software, or combination thereof supportive of input and output capabilities. For example, I/O module 908 may include hardware and/or software for capturing user input, including, but not limited to, a keyboard or keypad, a touch screen component (e.g., touch screen display), a receiver (e.g., an RF or infrared receiver), and/or one or more input buttons.

I/O module 908 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 900. For example, one or more applications 912 residing within storage device 906 may be configured to direct processor 904 to perform one or more processes or functions associated with middle ear analyzer subsystem 102, interface subsystem 104, and/or cochlear implant subsystem 106.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    maintaining, by an interface subsystem separate from and communicatively coupled to both a middle ear analyzer and a sound processor included in a cochlear implant system, mapping data representative of an association between a plurality of sound levels and a plurality of current levels and between a plurality of frequencies and a plurality of electrodes included in the cochlear implant system, the sound processor located external to a patient;
    receiving, by the interface subsystem, an acoustic signal transmitted by the middle ear analyzer to the interface subsystem by way of a stimulation probe that communicatively couples the middle ear analyzer and the system;
    detecting, by the interface subsystem, a sound level and a frequency of the acoustic signal; and
    synchronizing, by the interface subsystem, an operation of the middle ear analyzer and the cochlear implant system by
        identifying, based on the mapping data, a current level associated with the detected sound level and one or more electrodes associated with the detected frequency, the current level included in the plurality of current levels and the one or more electrodes included in the plurality of electrodes; and
        directing the cochlear implant system to apply electrical stimulation having the identified current level to one or more stimulation sites within patient by way of the identified one or more electrodes by transmitting, by way of a wired communication channel that couples the interface subsystem to the sound processor, control data representative of the identified current level and the identified one or more electrodes to the sound processor included in the cochlear implant system.

2. The method of claim 1, further comprising:
    detecting, by the interface subsystem, an increase in the sound level of the acoustic signal; and
    directing, by the interface subsystem, the cochlear implant system to dynamically increase the current level of the electrical stimulation in response to the increase in the sound level and in accordance with the mapping data.

3. The method of claim 1, embodied as computer-executable instructions on at least one non-transitory computer-readable medium.

4. A system comprising:
a middle ear analyzer subsystem configured to generate and transmit an acoustic signal by way of a stimulation probe; and
an interface subsystem separate from and communicatively coupled to the middle ear analyzer by way of the stimulation probe and to a sound processor located external to a patient and included in a cochlear implant subsystem, wherein the interface subsystem is configured to
maintain mapping data representative of an association between a plurality of sound levels and a plurality of current levels and between a plurality of frequencies and a plurality of electrodes,
receive the acoustic signal transmitted by the middle ear analyzer subsystem,
detect a sound level and a frequency of the acoustic signal, and
synchronize an operation of the middle ear analyzer subsystem and the cochlear implant subsystem by
identifying, based on the mapping data, a current level associated with the detected sound level and one or more electrodes associated with the detected frequency, the current level included in the plurality of current levels and the one or more electrodes included in the plurality of electrodes, and
directing the cochlear implant subsystem to apply electrical stimulation having the identified current level to one or more stimulation sites within the patient by way of the identified one or more electrodes by transmitting, by way of a wired communication channel that couples the interface subsystem to the sound processor, control data representative of the identified current level and the identified one or more electrodes to the sound processor included in the cochlear implant subsystem.

5. The system of claim 4, wherein:
the middle ear analyzer subsystem is further configured to
detect a change in an acoustic immittance that occurs in response to the application of the electrical stimulation by the cochlear implant, and
increase the sound level of the acoustic signal until the change in the acoustic immittance indicates an occurrence of a stapedius reflex; and
the interface subsystem is further configured to direct the cochlear implant subsystem to dynamically increase the current level of the electrical stimulation in response to the increase in the sound level and in accordance with the mapping data.

6. The system of claim 5, wherein the interface subsystem is further configured to designate a current level at which the stapedius reflex occurs as a most comfortable current level associated with the patient.

7. The system of claim 6, wherein the interface subsystem is further configured to present, within a graphical user interface, data representative of the most comfortable current level.

8. The system of claim 5, wherein the middle ear analyzer subsystem is further configured to present, within a graphical user interface, a graph representative of the change in the acoustic immittance that occurs as the sound level is increased.

9. The system of claim 4, wherein:
the middle ear analyzer subsystem is further configured to
detect a change in an acoustic immittance that occurs in response to the application of the electrical stimulation by the cochlear implant, and
increase the sound level of the acoustic signal until the sound level of the acoustic signal is equal to a predetermined maximum threshold level; and
the interface subsystem is further configured to direct the cochlear implant subsystem to dynamically increase the current level of the electrical stimulation in response to the increase in the sound level and in accordance with the mapping data.

10. The system of claim 9, wherein the interface subsystem is further configured to
receive, by way of a graphical user interface, user input representative of a sound level at which a stapedius reflex occurred during the application of the electrical stimulation;
determine, based on the user input and on the mapping data, a current level at which the stapedius reflex occurred; and
provide, by way of the graphical user interface, data representative of the current level at which the stapedius reflex occurred.

11. The system of claim 4, wherein the middle ear analyzer subsystem is further configured to operate in accordance with a contralateral stimulation mode while generating and transmitting the acoustic signal.

12. The system of claim 4, wherein the interface subsystem is further configured to facilitate, by way of a graphical user interface, user customization of the mapping data.

13. The system of claim 4, wherein:
the middle ear analyzer subsystem is further configured to generate and transmit an additional acoustic signal; and
the interface subsystem is further configured to
detect a sound level of the additional acoustic signal,
identify, based on the mapping data, an additional current level included in the plurality of current levels that is associated with the detected sound level of the additional acoustic signal,
receive user input identifying one or more electrodes, and
direct a cochlear implant subsystem to apply electrical stimulation having the additional identified current level to one or more stimulation sites within a patient by way of the one or more electrodes identified by the user input.

14. A system separate from and communicatively coupled to both a sound processor included in a cochlear implant system and a middle ear analyzer, the sound processor located external to a patient, the system comprising:
a mapping facility configured to maintain mapping data representative of an association between a plurality of sound levels and a plurality of current levels and between a plurality of frequencies and a plurality of electrodes;
a detection facility communicatively coupled to the mapping facility and configured to
receive an acoustic signal transmitted by the middle ear analyzer to the system by way of a stimulation probe that communicatively couples the middle ear analyzer and the system, and
detect a sound level and a frequency of the acoustic signal; and
a processing facility communicatively coupled to the mapping facility and to the detection facility and configured to synchronize an operation of the middle ear analyzer and the cochlear implant system by identifying, based on the mapping data, a current level associated with the detected sound level and one or more electrodes associated with the detected frequency, the current level included in the plurality of current levels and the one or more electrodes included in the plurality of electrodes, and directing the cochlear implant system to apply electrical stimulation having the identified current level to one or more stimulation sites within the patient by way of the identified one or more electrodes by transmitting, by way of a wired communication channel that couples the system to the sound processor, control data representative of the identified current level and the identified one or more electrodes to the sound processor included in the cochlear implant system.

15. The system of claim 14, wherein:
the detection facility is further configured to detect an increase in the sound level of the acoustic signal; and
the processing facility is further configured to direct the cochlear implant system to dynamically increase the current level of the electrical stimulation in response to the increase in the sound level and in accordance with the mapping data.

16. The system of claim 14, wherein the electrical stimulation causes a stapedius reflex to occur, and wherein the processing facility is further configured to:
designate the current level as a most comfortable current level associated with the patient; and
present, within a graphical user interface, data representative of the most comfortable current level.

17. The system of claim 14, wherein the processing facility is further configured to:
receive, by way of a graphical user interface, user input representative of a sound level at which a stapedius reflex occurred during the application of the electrical stimulation;

determine, based on the user input and on the mapping data, a current level at which the stapedius reflex occurred; and
provide, by way of the graphical user interface, data representative of the current level at which the stapedius reflex occurred.

18. A system separate from and communicatively coupled to both a sound processor included in a cochlear implant system and a middle ear analyzer, the sound processor located external to a patient, the system comprising:
a mapping facility configured to maintain mapping data representative of an association between a plurality of sound levels and a plurality of current levels;
a detection facility communicatively coupled to the mapping facility and configured to
receive an acoustic signal transmitted by the middle ear analyzer to the system by way of a stimulation probe that communicatively couples the middle ear analyzer and the system, and
detect a sound level of the acoustic signal transmitted by the middle ear analyzer; and
a processing facility communicatively coupled to the mapping facility and to the detection facility and configured to synchronize an operation of the middle ear analyzer and the cochlear implant system by
identifying, based on the mapping data, a current level included in the plurality of current levels that is associated with the detected sound level,
receiving user input identifying one or more electrodes, and
directing a cochlear implant system to apply electrical stimulation having the identified current level to one or more stimulation sites within the patient by way of the identified one or more electrodes by transmitting, by way of a wired communication channel that couples the system to the sound processor, control data representative of the identified current level and the identified one or more electrodes to the sound processor included in the cochlear implant system.

* * * * *